(12) United States Patent
Park et al.

(10) Patent No.: US 11,844,652 B2
(45) Date of Patent: Dec. 19, 2023

(54) ULTRASOUND DIAGNOSIS APPARATUS AND METHOD OF OPERATING THE SAME

(71) Applicant: SAMSUNG MEDISON CO., LTD., Hongcheon-gun (KR)

(72) Inventors: Sungchan Park, Seongnam-si (KR); Jaehyun Kwon, Seongnam-si (KR); Jungho Kim, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 858 days.

(21) Appl. No.: 16/693,777

(22) Filed: Nov. 25, 2019

(65) Prior Publication Data
US 2020/0187911 A1 Jun. 18, 2020

Related U.S. Application Data

(60) Provisional application No. 62/779,582, filed on Dec. 14, 2018.

(30) Foreign Application Priority Data

Jun. 19, 2019 (KR) .................. 10-2019-0073105

(51) Int. Cl.
*A61B 8/08* (2006.01)
*G06T 5/50* (2006.01)
*A61B 8/00* (2006.01)

(52) U.S. Cl.
CPC ............ *A61B 8/5207* (2013.01); *A61B 8/461* (2013.01); *A61B 8/5269* (2013.01); *A61B 8/587* (2013.01);
(Continued)

(58) Field of Classification Search
CPC ............ G01S 7/52046; G01S 7/52026; A61B 8/5269; A61B 8/5207; G06T 2207/10132
See application file for complete search history.

(56) References Cited

U.S. PATENT DOCUMENTS 4,561,019 A 12/1985 Lizzi et al.
5,404,883 A 4/1995 Freedman et al.
(Continued)

FOREIGN PATENT DOCUMENTS

| JP | 7-51270 A | 2/1995 |
|---|---|---|
| JP | 2015-208638 A | 11/2015 |
| KR | 10-2016-0139163 A | 12/2016 |

OTHER PUBLICATIONS

"Samsung Unveils a New Ultrasound System 'Hera W10' Powered by Beamforming Technology at ISUOG World Congress 2018", Samsung Newsroom, Oct. 21, 2018. (12 pages total) (Samsung Medison Co., Ltd.).

(Continued)

*Primary Examiner* — Angela M Hoffa
*Assistant Examiner* — Younhee Choi
(74) *Attorney, Agent, or Firm* — Sughrue Mion, PLLC

(57) ABSTRACT

A method of operating an ultrasound diagnosis apparatus includes: acquiring a plurality of frequency band images respectively having different frequency bands based on an ultrasound signal corresponding to an object; determining weights respectively for the plurality of frequency band images based on brightness levels of regions including the object in each of the plurality of frequency band images; synthesizing the plurality of frequency band images based on the weights for the plurality of frequency band images; and displaying a synthetic ultrasound image of the object, generated as a result of the synthesizing.

17 Claims, 13 Drawing Sheets

(52) U.S. Cl.
CPC ...... *G06T 5/50* (2013.01); *G06T 2207/10132* (2013.01)

(56) References Cited

U.S. PATENT DOCUMENTS

| | | | |
|---|---|---|---|
| 6,018,596 | A | 1/2000 | Wilkinson |
| 9,460,499 | B2 | 10/2016 | McLaughlin et al. |
| 10,143,432 | B2 | 12/2018 | Jeong et al. |
| 10,178,977 | B2 | 1/2019 | Kato et al. |
| 2004/0187583 | A1* | 9/2004 | Ogawa ............... G01S 7/52046 73/628 |
| 2012/0078103 | A1* | 3/2012 | Tashiro ............... A61B 8/463 600/443 |
| 2016/0019702 | A1* | 1/2016 | Park ............... G06T 11/60 382/131 |
| 2017/0053396 | A1* | 2/2017 | Zhai ............... G06T 7/0012 |

OTHER PUBLICATIONS

Samsung, "HERA W10—Introduction to Samsung Healthcare", v0.76.Cine, Dec. 14, 2018. (23 pages total).

"28th World Congress on Ultrasound in Obstetrics and Gynecology", Oct. 20, 2018-Oct. 24, 2018, Singapore. (1 page total).

"New Momentum of Imaging HERA W10", Samsung Medison Co., Ltd., 2019 (8 pages total).

"Only for New Experiences at USUOG World Congress", 28$^{TH}$ World Congress on Ultrasound in Obstetrics and Gynecology, Samsung, 2018 (18 pages total).

Communication dated Jun. 15, 2020 issued by the European Patent Office in Application No. 19210136.8.

Xiao, Y., et al., "High-Dynamic-Range Ultrasound: Application For Imaging Tendon Pathology", Ultrasound in Medicine & Biology, vol. 44, No. 7, 2018, pp. 1525-1532.

Communication dated Feb. 22, 2023, issued by the European Patent Office in counterpart European Application No. 19 210 136.8.

* cited by examiner

FIG. 7
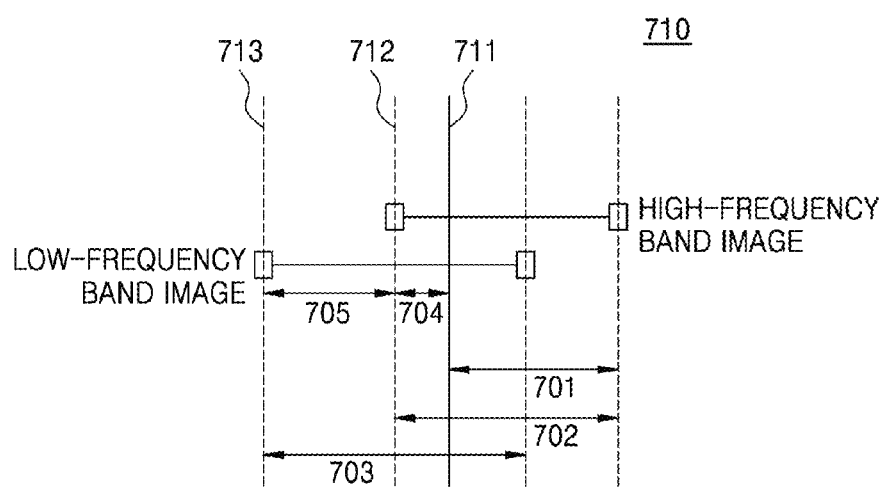
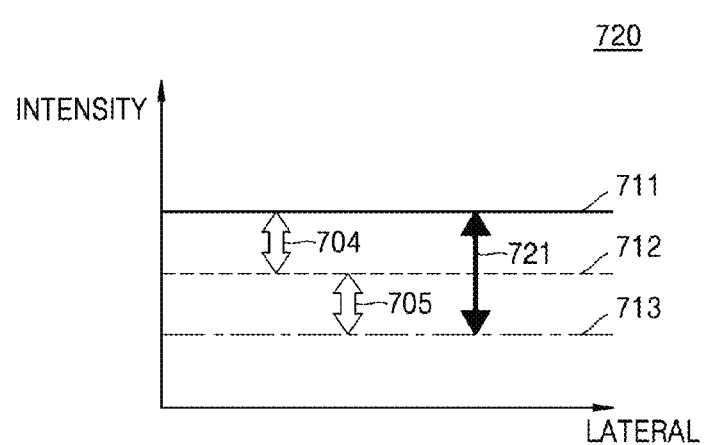

811: $I_1$ — cells $i_{111}$ ... $i_{144}$

812: $I_2$ — cells $i_{211}$ ... $i_{244}$

813: $I_N$ — cells $i_{N11}$ ... $i_{N44}$

825: $I$ — cells $I_{11}$ ... $I_{44}$

820:
$$I_{11} = i_{111} \times W_{111} + i_{211} \times W_{211} + i_{311} \times W_{311} + \cdots + i_{N11} \times W_{N11} \quad (1)$$
$$I_{12} = i_{112} \times W_{112} + i_{212} \times W_{212} + i_{312} \times W_{312} + \cdots + i_{N12} \times W_{N12} \quad (2)$$
$$\vdots$$
$$I_{44} = i_{144} \times W_{144} + i_{244} \times W_{244} + i_{344} \times W_{344} + \cdots + i_{N44} \times W_{N44} \quad (3)$$

ULTRASOUND DIAGNOSIS APPARATUS AND METHOD OF OPERATING THE SAME

CROSS-REFERENCE TO RELATED APPLICATION(S)

This application claims the benefit of U.S. Provisional Application No. 62/779,582, filed on Dec. 14, 2018, in the US Patent Office and Korean Patent Application No. 10-2019-0073105, filed on Jun. 19, 2019, in the Korean Intellectual Property Office, the disclosures of which are incorporated herein in their entireties by reference.

BACKGROUND

1. Field

The disclosure relates to an ultrasound diagnosis apparatus and a method of operating the same.

2. Description of Related Art

Ultrasound diagnosis apparatuses transmit, to an object, ultrasound signals generated by transducers of a probe and detect information about signals reflected from the object, thereby obtaining at least one image of an internal part, for example, soft tissue or blood flow, of the object.

SUMMARY

Provided are ultrasound diagnosis apparatuses capable of obtaining a sharp ultrasound image by respectively setting weights corresponding to brightness levels or detail levels for regions of an object in a plurality of frequency band images and synthesizing the plurality of frequency band images or a plurality of steer images according to the set weights.

Additional aspects will be set forth in part in the description which follows and, in part, will be apparent from the description, or may be learned by practice of the presented embodiments of the disclosure.

In accordance with an aspect of the disclosure, a method of operating an ultrasound diagnosis apparatus includes: acquiring a plurality of frequency band images respectively having different frequency bands based on an ultrasound signal corresponding to an object; determining weights respectively for the plurality of frequency band images based on brightness levels of regions including the object in each of the plurality of frequency band images; synthesizing the plurality of frequency band images based on the weights for the plurality of frequency band images; and displaying a synthetic ultrasound image of the object generated as a result of the synthesizing.

In accordance with another aspect of the disclosure, a method of operating an ultrasound diagnosis apparatus includes: acquiring a plurality of steer images based on an ultrasound signal corresponding to an object and acquired according to a beam steering operation by a probe; acquiring a base image representing brightness levels of regions of the object and a detail image representing details of the regions of the object by performing spatial filtering on each of the plurality of steer images; setting weights of base images respectively for the plurality of steer images based on the brightness levels for the regions of the object and synthesizing the base images; setting weights for detail images respectively for the plurality of steer images based on detail levels for the regions of the object and synthesizing the detail images; and displaying a synthetic steer image obtained by combining a synthetic base image acquired by the synthesizing of the base images with a synthetic detail image acquired by the synthesizing of the detail images.

In accordance with another aspect of the disclosure, a computer program is stored on a medium for executing, in an ultrasound diagnosis apparatus, a method of operating the ultrasound diagnosis apparatus.

In accordance with another aspect of the disclosure, an ultrasound diagnosis apparatus includes: a probe configured to transmit an ultrasound signal to an object and receive an ultrasound signal reflected from the object; a processor configured to acquire a plurality of frequency band images respectively having different frequency bands based on the reflected ultrasound signal, determine weights respectively for the plurality of frequency band images based on brightness levels of regions including the object in each of the plurality of frequency band images, and generate a synthetic ultrasound image of the object by synthesizing the plurality of frequency band images based on the weights for the plurality of frequency band images; and a display displaying the synthetic ultrasound image.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 7 is a diagram for explaining a brightness range that is expanded by using high- and low-frequency band images in generating an ultrasound image, according to an embodiment;

FIG. 8 is a diagram for explaining a process, performed by an ultrasound diagnosis apparatus, of respectively determining weights for a plurality of frequency band images and synthesizing the plurality of frequency band images according to the weights, according to an embodiment;

DETAILED DESCRIPTION

Figure 1:
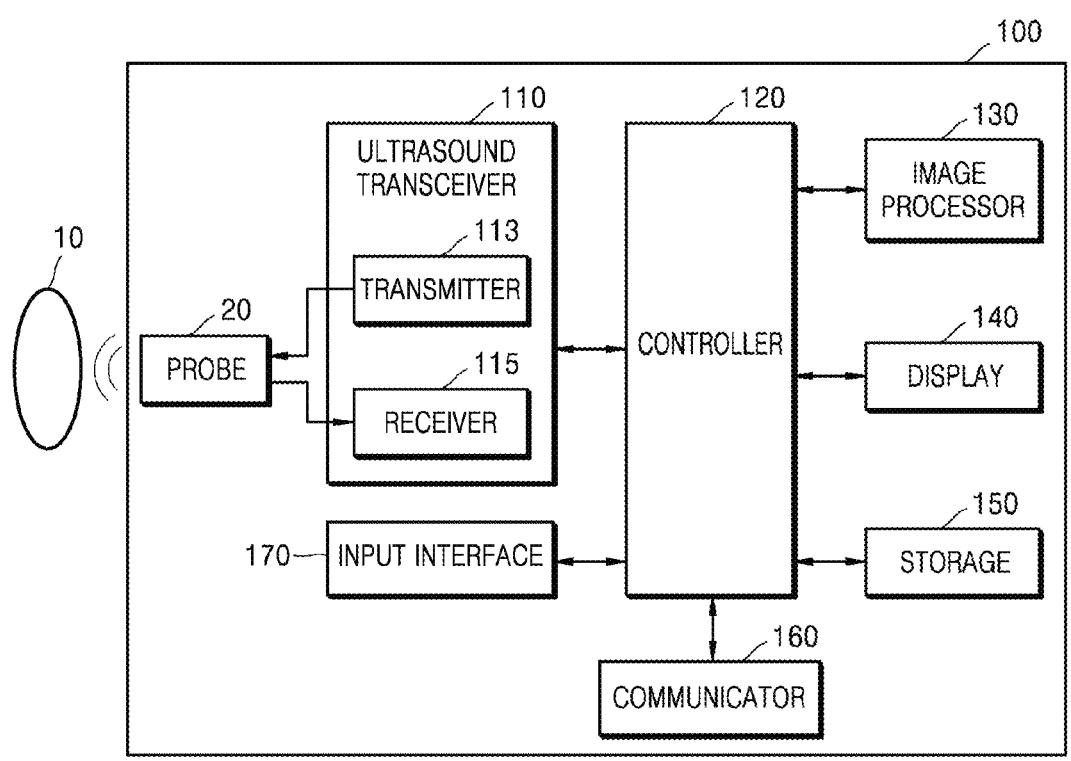
FIG. 1 is a block diagram of a configuration of an ultrasound diagnosis apparatus according to an embodiment.

Certain exemplary embodiments are described in greater detail below with reference to the accompanying drawings. The present specification describes principles of the present disclosure and sets forth embodiments thereof to clarify the scope of the present disclosure and to allow those of ordinary skill in the art to implement the embodiments. The present embodiments may have different forms and should not be construed as being limited to the descriptions set forth herein.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail. Like reference numerals refer to like elements throughout. The present specification does not describe all components in the embodiments, and common knowledge in the art or the same descriptions of the embodiments will be omitted below. Terms such as "part" and "portion" used herein denote those that may be embodied by software or hardware. According to exemplary embodiments, a plurality of parts or portions may be embodied by a single unit or element, or a single part or portion may include a plurality of elements. Expressions such as "at least one of," when preceding a list of elements, modify the entire list of elements and do not modify the individual elements of the list. Hereinafter, the principles and embodiments of the present disclosure will be described in detail with reference to the accompanying drawings.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

FIG. 1 is a block diagram illustrating a configuration of an ultrasound diagnosis apparatus 100, i.e., a diagnostic apparatus, according to an exemplary embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus that is portable, moveable, mobile, or hand-held. Examples of the portable-type ultrasound diagnosis apparatus may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control an ultrasound receiver 115 to generate ultrasound data by converting reception signals received from the probe 20 from analog to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

Figure 2:
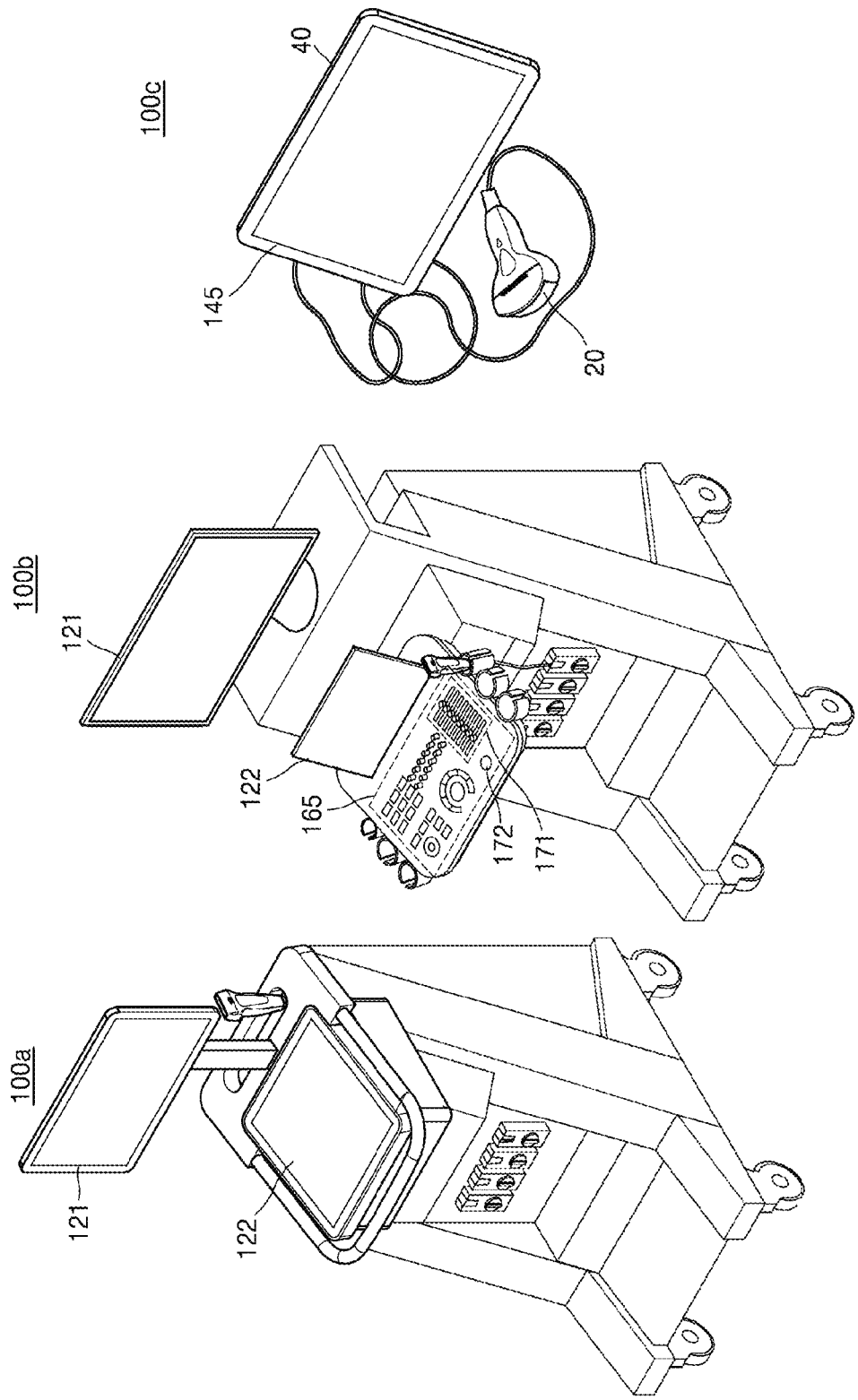
FIGS. 2A through 2C illustrate ultrasound diagnosis apparatuses according to embodiments.

An example of the ultrasound diagnosis apparatus 100 according to the present exemplary embodiment is described below with reference to FIGS. 2A, 2B, and 2C.

FIGS. 2A, 2B, and 2C are diagrams illustrating an ultrasound diagnosis apparatus according to an exemplary embodiment.

Referring to FIGS. 2A and 2B, the ultrasound diagnosis apparatus 100a or 100b may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100a or 100b. The main display 121 and the sub-display 122 may provide graphical user interfaces (GUI), thereby receiving user's inputs of data to control the ultrasound diagnosis apparatus 100a or 100b. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100a or 100b may control the display of the ultrasound image on the main display 121 by using the input control data.

Referring to FIG. 2B, the ultrasound diagnosis apparatus 100b may include a control panel 165. The control panel 165 may include buttons, trackballs, jog switches, or knobs, and may receive data to control the ultrasound diagnosis apparatus 100b from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100b may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100c may include a portable device. An example of the portable ultrasound diagnosis apparatus 100c may include smart phones including probes and applications, laptop computers, personal digital assistants (PDAs), or tablet PCs, but an exemplary embodiment is not limited thereto.

The ultrasound diagnosis apparatus 100c may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100c, and a GUI.

Figure 3:
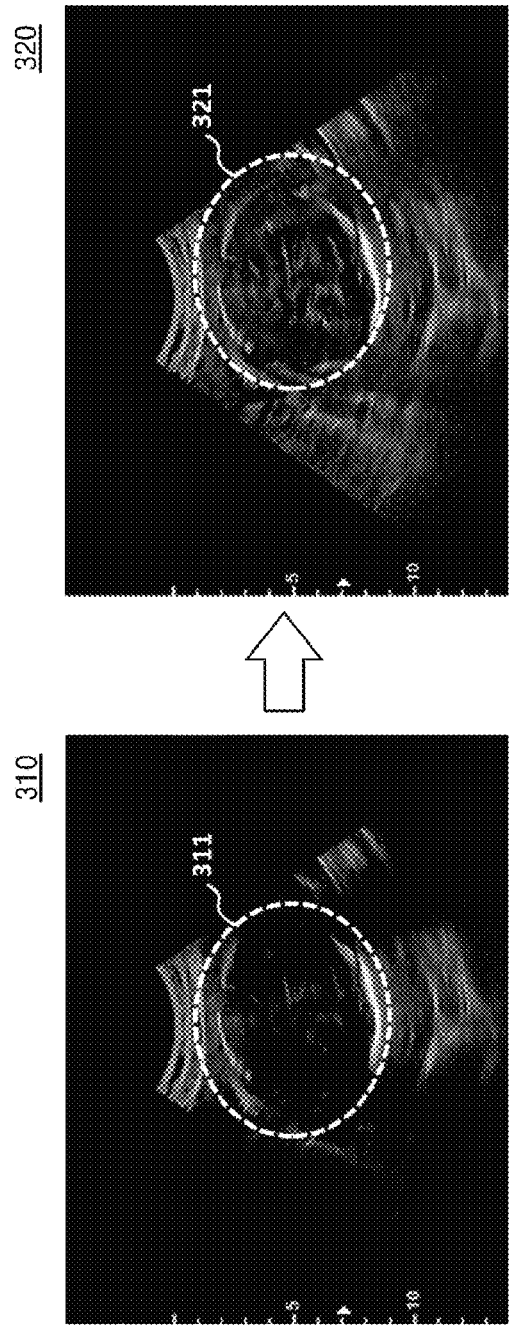
FIG. 3 is a diagram for explaining a process of performing image processing on a shadow region in an ultrasound image by using an ultrasound diagnosis apparatus, according to an embodiment.

FIG. 3 is a diagram for explaining a process of performing image processing on a shadow region in an ultrasound image by using an ultrasound diagnosis apparatus, according to an embodiment.

Referring to an image 310 of FIG. 3, the ultrasound diagnosis apparatus 100 may transmit an ultrasound signal to an object and receive an ultrasound signal reflected from the object. The ultrasound diagnosis apparatus 100 may obtain an ultrasound image of the object based on the reflected ultrasound signal and display the ultrasound image.

When the object has a high medium rigidity, as an ultrasound signal travels deeper into the object, the magnitude of the ultrasound signal rapidly decreases. Furthermore, as the ultrasound signal has more high-frequency components and travels deeper into the object, the magnitude of the ultrasound signal decreases. In other words, as an attenuation coefficient of the ultrasound signal increases, as shown in the image 310 of FIG. 3, more portions of an ultrasound image may appear dark, or the ultrasound image may have a shadow region 311 in which a region of the object is invisible.

The shadow region 311 in the ultrasound image has a lower brightness level than a predetermined brightness level or a higher noise level than a predetermined noise level. Thus, the ultrasound diagnosis apparatus 100 may clearly display the shadow region 311 by using image information regarding a low-frequency band image.

The ultrasound diagnosis apparatus 100 may acquire image information regarding a region corresponding to the shadow region 311 from the low-frequency band image of the object. The ultrasound diagnosis apparatus 100 may improve the sharpness of the shadow region 311 by assigning a high weight to the image information regarding the low-frequency band image and synthesizing the low-frequency band image with a high-frequency band image.

Referring to an image 320 of FIG. 3, a region in the image 320 may be sharper than the shadow region 311 in the image 310.

Figure 4:
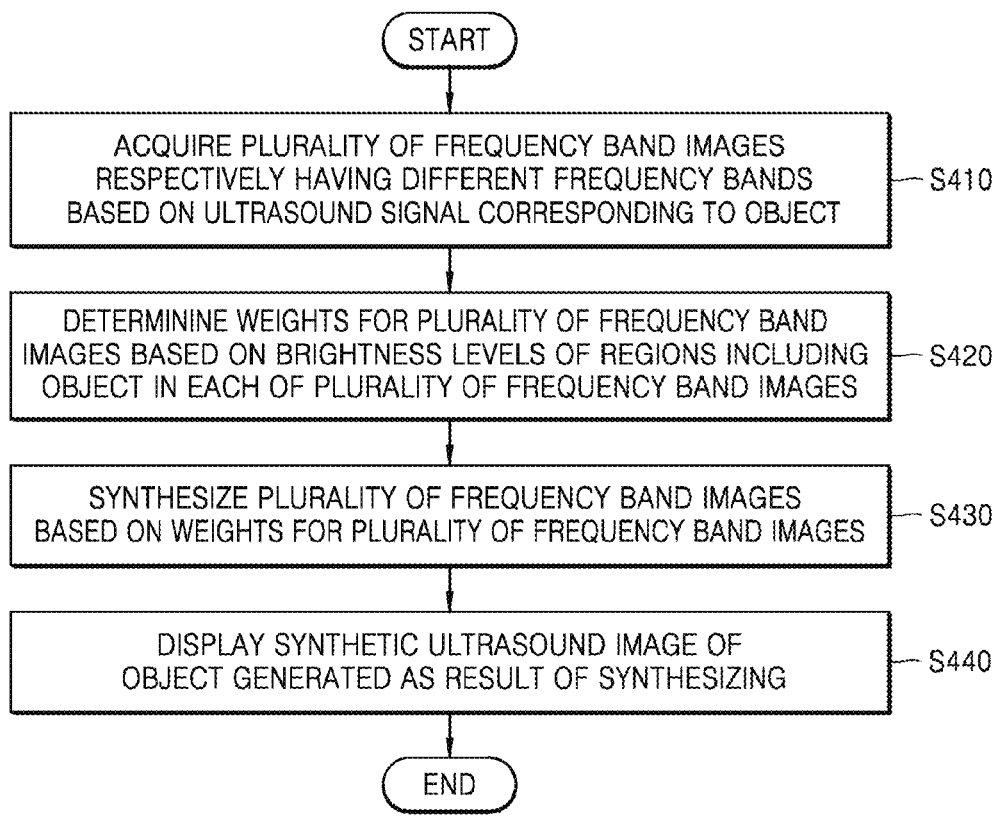
FIG. 4 is a flowchart of a method of operating an ultrasound diagnosis apparatus, according to an embodiment.

FIG. 4 is a flowchart of a method of operating the ultrasound diagnosis apparatus 100, according to an embodiment.

Referring to FIG. 4, the ultrasound diagnosis apparatus 100 may acquire a plurality of frequency band images respectively having different frequency bands based on an ultrasound signal corresponding to an object (S410).

For example, the ultrasound diagnosis apparatus 100 may decompose the ultrasound signal according to a plurality of frequency bands. The ultrasound diagnosis apparatus 100 may acquire, based on the decomposed ultrasound signal, a high-frequency band image corresponding to a predetermined high frequency band and a low-frequency band image corresponding to a predetermined low frequency band.

The ultrasound diagnosis apparatus 100 may respectively determine weights for the plurality of frequency band images based on brightness values of regions including the object in each of the plurality of frequency band images (S420).

For example, the ultrasound diagnosis apparatus 100 may detect, in a high-frequency band image, a shadow region having a lower brightness level than a predetermined brightness level and a higher noise level than a predetermined noise level. The ultrasound diagnosis apparatus 100 may acquire image information regarding a first region corresponding to the shadow region from a low-frequency band image. The ultrasound diagnosis apparatus 100 may set a weight for image information regarding the first region to be higher than a weight for image information regarding the shadow region in the high-frequency band image.

Furthermore, the ultrasound diagnosis apparatus 100 may set a weight for image information regarding a non-shadow region in the high-frequency band image to be higher than a weight for image information regarding a second region in the low-frequency band image corresponding to the non-shadow region.

For example, the ultrasound diagnosis apparatus 100 may acquire a base image representing brightness levels for regions of the object and a detail image representing details of the regions of the object by performing spatial filtering on each of the plurality of frequency band images. The ultrasound diagnosis apparatus 100 may set, based on brightness levels for the regions of the object, a weight for a base image in each of a plurality of frequency bands. Furthermore, the ultrasound diagnosis apparatus 100 may set, based on detail levels of the regions of the object, a weight for a detail image in each of the plurality of frequency bands. A process, performed by the ultrasound diagnosis apparatus 100, of respectively setting weights for a base image and a detail image and obtaining a synthetic ultrasound image based on the weights will be described in more detail below with reference to FIGS. 6 through 9.

For example, the ultrasound diagnosis apparatus 100 may receive, via a UI device, an input of adjusting a strength of a weight for image information regarding a low-frequency band image among a plurality of frequency band images. The ultrasound diagnosis apparatus 100 may adjust, based on the input for adjusting a strength of a weight, a weight for image information regarding a low-frequency band image.

The ultrasound diagnosis apparatus 100 may synthesize the plurality of frequency band images based on the weights therefor (S430).

For example, the ultrasound diagnosis apparatus 100 may synthesize base images in the plurality of frequency bands according to weights respectively assigned to the base images. For example, a weight may be set within a range of 0 to 1. The weights of the base images may be added together to equal 1. Furthermore, a weight may be set for each region in a base image. Furthermore, a weight may be set within a range of 0% to 100%. The ultrasound diagnosis apparatus 100 may respectively multiply weights assigned to the base images by brightness values of the base images to acquire brightness values to which the weights have been applied. The ultrasound diagnosis apparatus 100 may acquire a synthetic base image by adding together the brightness values of to which the corresponding weights have been applied. Furthermore, the ultrasound diagnosis apparatus 100 may acquire a synthetic base image by outputting maximum absolute brightness values. For example, the ultrasound diagnosis apparatus 100 may determine a brightness value having a maximum absolute value among brightness values for each region of a base image and acquire a synthetic base image by synthesizing regions with maximum absolute brightness values.

Furthermore, the ultrasound diagnosis apparatus 100 may synthesize detail images in a plurality of frequency bands according to weights respectively assigned to the detail images. Detail images may be synthesized in the same manner that the base images are synthesized.

The ultrasound diagnosis apparatus 100 may obtain a synthetic ultrasound image by combining a synthetic base image with a synthetic detail image.

For example, the ultrasound diagnosis apparatus 100 may synthesize high- and low-frequency band images based on a weight for image information regarding the low-frequency band image, which is adjusted according to a user input.

The ultrasound diagnosis apparatus 100 may display a synthetic ultrasound image of the object generated as a result of the synthesis (S440).

The ultrasound diagnosis apparatus 100 may display the synthetic ultrasound image and an original ultrasound image obtained based on the ultrasound signal. The ultrasound diagnosis apparatus 100 may display a result of comparing a sharpness or noise between the synthetic and original ultrasound images.

The ultrasound diagnosis apparatus 100 may respectively set weights corresponding to brightness levels or detail levels for regions of the object in a plurality of frequency band images and synthesize the plurality of frequency band images, thereby obtaining a sharp ultrasound image. Thus, the ultrasound diagnosis apparatus 100 may clearly display dark and bright regions in an ultrasound image. Furthermore, the ultrasound diagnosis apparatus 100 may increase uniformity of an ultrasound image by compensating brightness for regions of the object.

Figure 5:
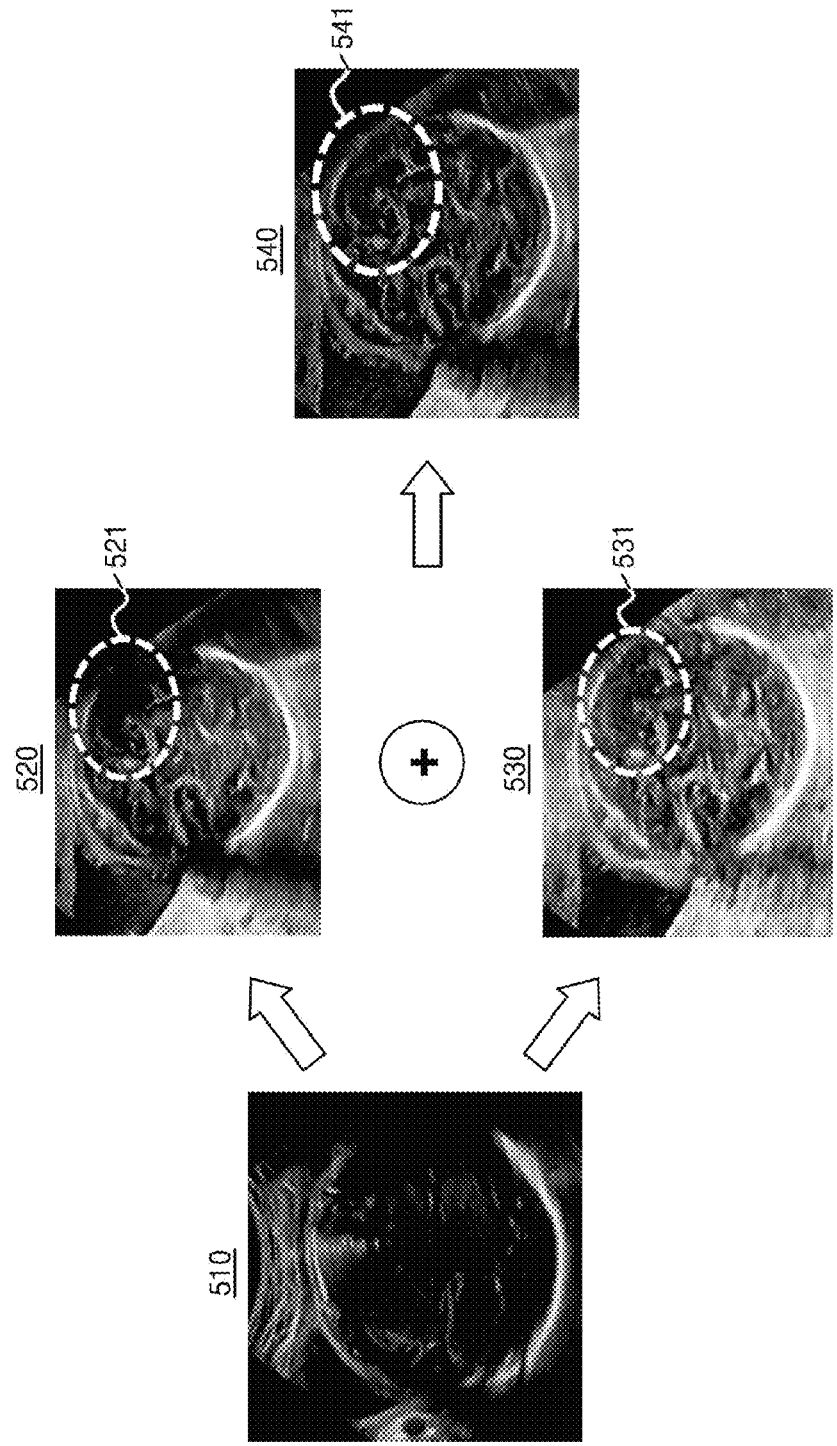
FIG. 5 is a diagram for explaining a process, performed by an ultrasound diagnosis apparatus, of performing image processing by using high- and low-frequency band images, according to an embodiment.

FIG. 5 is a diagram for explaining a process, performed by the ultrasound diagnosis apparatus 100, of performing image processing by using high- and low-frequency band images, according to an embodiment.

The ultrasound diagnosis apparatus 100 may transmit an ultrasound signal to an object and receive an ultrasound signal reflected from the object. The ultrasound diagnosis apparatus 100 may obtain an ultrasound image 510 base on the reflected ultrasound signal and display the ultrasound image 510.

Because a shadow region exists in the ultrasound image 510, the user may input a command that instructs the ultrasound diagnosis apparatus 100 to perform a task of correcting an image of the shadow region. The ultrasound diagnosis apparatus 100 may perform the task of correcting an image of the shadow region according to the user's command. Furthermore, the ultrasound diagnosis apparatus 100 may determine whether the shadow region exists in the ultrasound image 510 displayed via the ultrasound diagnosis apparatus 100 When the shadow region exists therein, the ultrasound diagnosis apparatus 100 may perform the task of correcting an image of the shadow region.

For example, the ultrasound diagnosis apparatus 100 may acquire high- and low-frequency band images 520 and 530 for the ultrasound image 510. In detail, the ultrasound diagnosis apparatus 100 may acquire high-frequency band image data by passing an ultrasound signal through a high-pass filter that allows only a signal in a predetermined high frequency band to pass. The ultrasound diagnosis apparatus 100 may then acquire the high-frequency band image 520 based on the high-frequency band image data. Furthermore, the ultrasound diagnosis apparatus 100 may acquire low-frequency band image data by passing the ultrasound signal through a low-pass filter that allows only a signal in a predetermined low frequency band to pass. The ultrasound diagnosis apparatus 100 may then acquire the low-frequency band image 530 based on the low-frequency band image data.

The high-frequency band image 520 may have a higher resolution than that of the low-frequency band image 530. Thus, details of the object represented in the low-frequency band image 530 may be compensated by details of the object represented in the high-frequency band image 520.

Furthermore, because an ultrasound signal in a low frequency band suffers less attenuation than an ultrasound signal in a high frequency band, the ultrasound signal in the low frequency band may travel deeper into the object than the ultrasound signal in the high frequency band. Thus, the low-frequency band image 530 may show a deep region of the object compared to the high-frequency band image 520. Thus, a deep region of the object that is not clearly represented in the high-frequency band image 520 may be complemented by using image information regarding the low-frequency band image 530.

The ultrasound diagnosis apparatus 100 may detect a shadow region 521 in the high-frequency band image 520. The ultrasound diagnosis apparatus 100 may acquire image information regarding a region 531 corresponding to the shadow region 521 from the low-frequency band image 530. The ultrasound diagnosis apparatus 100 may compensate a brightness or details of the shadow region 521 in the high-frequency band image 520 by using image information regarding the region 531 in the low-frequency band image 530.

In detail, the ultrasound diagnosis apparatus 100 may set a weight for image information regarding the region 531 in the low-frequency band image 530 to be higher than a weight for image information regarding the shadow region 521 in the high-frequency band image 520 and synthesize the high- and low-frequency band images 520 and 530 according to the weights. As a result of the synthesis, the ultrasound diagnosis apparatus 100 may obtain a synthetic ultrasound image 540.

Referring to the synthetic ultrasound image 540 of FIG. 5, the object in the synthetic ultrasound image 540 may be shown more clearly than that in the ultrasound image 510. Furthermore, a portion of the object depicted in the region 541 of the synthetic ultrasound image 540 may appear clearer than the corresponding portion of the object in the shadow region 521 of the high-frequency band image 520. Furthermore, there is reduced noise in the region 541 of the synthetic ultrasound image 540, compared to in the region 531 of the low-frequency band image 530. In other words, the ultrasound diagnosis apparatus 100 may prevent an increase in noise in the region 541 of the synthetic ultrasound image 540 by using the low-frequency band image 530, Furthermore, by using the low-frequency band image 530 with a low attenuation coefficient, the ultrasound diagnosis apparatus 100 may distinguish a dark region having a high attenuation from a dark region having a low reflection coefficient and prevent an excessive change in brightness of a region with a low reflection coefficient.

Figure 6:
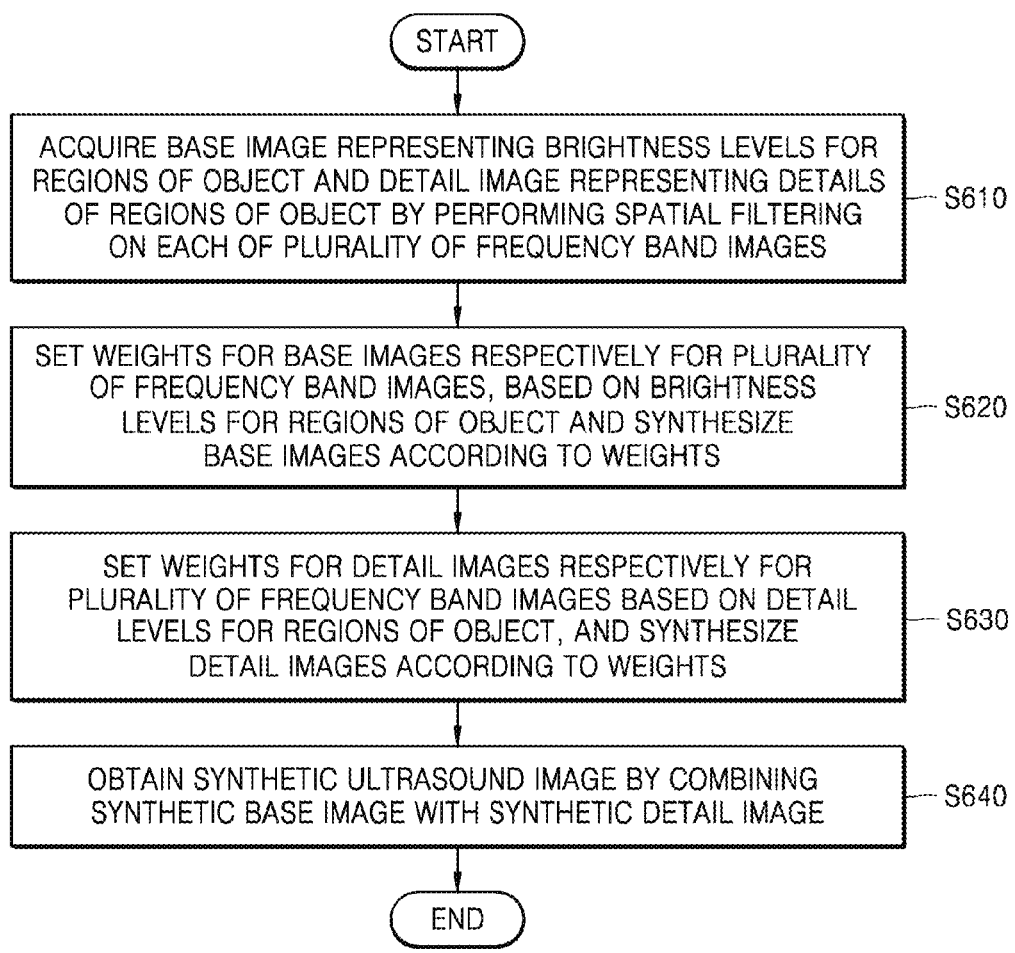
FIG. 6 is a flowchart of a method of operating an ultrasound diagnosis apparatus, according to an embodiment.

FIG. 6 is a flowchart of a method of operating the ultrasound diagnosis apparatus 100, according to an embodiment.

Referring to FIG. 6, the ultrasound diagnosis apparatus 100 may acquire a base image representing brightness levels for regions of the object and a detail image representing details of the regions of the object by performing spatial filtering on each of the plurality of frequency band images (S610).

The ultrasound diagnosis apparatus 100 may respectively set weights for base images for the plurality of frequency band images based on the brightness levels for the regions of the object, and synthesize the base images according to the weights (S620).

For example, with respect to a bright region having a brightness level that is greater than or equal to a first level among brightness levels lower than a first reference level used as a reference in representing the brightness levels for the regions of the object, the ultrasound diagnosis apparatus 100 may set a weight for image information regarding a base image for a high-frequency band image to be higher than a weight for image information regarding a base image for a low-frequency band image.

Furthermore, with respect to a dark region having a brightness level that is less than the first level among the brightness levels lower than the first reference level, the ultrasound diagnosis apparatus 100 may set a weight for image information regarding a base image for a low-frequency band image to be higher than a weight for image information regarding a base image for a high-frequency band image.

The ultrasound diagnosis apparatus 100 may respectively set weights for detail images for the plurality of frequency band images based on detail levels for the regions of the object, and synthesize the detail images according to the weights (S630).

For example, with respect to a bright region having a detail level that is greater than or equal to a second level among detail levels lower than a second reference level used as a reference in representing sharpness levels for the regions of the object, the ultrasound diagnosis apparatus 100 may set a weight for image information regarding a detail image for a high-frequency band image to be higher than a weight for image information regarding a detail image for a low-frequency band image.

Furthermore, with respect to a dark region having a detail level that is less than the second level among the detail levels lower than the second reference level, the ultrasound diagnosis apparatus 100 may set a weight for image information regarding a detail image for a low-frequency band image to be higher than a weight for image information regarding a detail image for a high-frequency band image.

The ultrasound diagnosis apparatus 100 may obtain a synthetic ultrasound image by combining a synthetic base image with a synthetic detail image (S640). The ultrasound diagnosis apparatus 100 may display the synthetic ultrasound image.

FIG. 7 is a diagram for explaining a brightness range that is expanded by using high- and low-frequency band images when generating an ultrasound image, according to an embodiment.

Referring to an image 710 of FIG. 7, a brightness range for an ultrasound image generated by the ultrasound diagnosis apparatus 100 may be a first range 701. Only a bright region having a brightness greater than or equal to a reference level 711 may be represented in the ultrasound image while a region having a brightness less than the reference level 711 may not be represented therein.

In addition, brightness ranges for high- and low-frequency band images may be second and third ranges 702 and 703, respectively. The ultrasound diagnosis apparatus 100 may acquire image information regarding the region having brightness less than the reference level 711 from the high- and low-frequency band images.

For example, the ultrasound diagnosis apparatus 100 may acquire, from the high-frequency band image, image information regarding a region having a brightness range 704 that is greater than or equal to a first level 712 but less than the reference level 711. Furthermore, the ultrasound diagnosis apparatus 100 may acquire, from the low-frequency band image, image information regarding a region having a brightness range 705 that is greater than or equal to a second level 713 but less than the first level 712.

The high-frequency band image has a higher resolution than that of the low-frequency band image. Thus, when generating a region having a brightness that falls within the brightness range 704, the ultrasound diagnosis apparatus 100 may set a weight for image information regarding the high-frequency band image to be higher than a weight for image information regarding the low-frequency band image and synthetize the high- and low-frequency band images according to the set weights.

Furthermore, the low-frequency band image contains image information to the extent of a deep region of an object compared to the high-frequency band image. Thus, when generating a region having a brightness that falls within the brightness range 705, the ultrasound diagnosis apparatus 100 may set a weight for image information regarding the low-frequency band image to be higher than a weight for image information regarding the high-frequency band image and synthetize the high- and low-frequency band images according to the set weights.

Referring to a graph 720 of FIG. 7, when the ultrasound diagnosis apparatus 100 displays an ultrasound image generated based on an ultrasound signal without performing a process for correcting a shadow region in the ultrasound image, a brightness range available for the ultrasound image may be a range that is greater than or equal to the reference level 711. The intensity in the graph 720 represents the brightness.

Otherwise, when the ultrasound diagnosis apparatus 100 performs a process for correcting a shadow region in an ultrasound image, the ultrasound diagnosis apparatus 100 may generate an ultrasound image having the brightness range 705 that is greater than or equal to the second level 713 but less than the first level 712 from an image having the brightness range 704 that is greater than or equal to the first level 712 but less than the reference level 711. Thus, a brightness range available for the ultrasound image may be expanded beyond the range greater than or equal to the reference level 711 into the brightness range 721.

In other words, the ultrasound diagnosis apparatus 100 may expand a brightness range available for the ultrasound image by using the high- and low-frequency band images.

FIG. 8 is a diagram for explaining a process, performed by the ultrasound diagnosis apparatus 100, of respectively determining weights for a plurality of frequency band images and synthesizing the plurality of frequency band images according to the weights, according to an embodiment.

Referring to an image 810 of FIG. 8, the ultrasound diagnosis apparatus 100 may acquire the number N of frequency band images having different frequency bands based on an ultrasound signal corresponding to an object. In detail, the ultrasound diagnosis apparatus 100 may acquire a first frequency band image 811, a second frequency band image 812 having a second frequency band, . . . , and an N-th frequency band image 813 having an N-th frequency band.

The ultrasound diagnosis apparatus 100 may acquire brightness values of a plurality of regions into which each of the N frequency band images is segmented. Referring to FIG. 8, $i_{kml}$ represents a brightness value at m-th row and l-th column in a k-th frequency band image. As shown in FIG. 8, the ultrasound diagnosis apparatus 100 may display each of the N frequency band images as a brightness map representing brightness values of a plurality of regions.

Referring to an image 820 of FIG. 8, the ultrasound diagnosis apparatus 100 may acquire brightness values of a plurality of regions in a synthetic ultrasound image 825. For example, the ultrasound diagnosis apparatus 100 may respectively determine weights for the N frequency band images based on brightness values of a plurality of regions in each of the N frequency band images and acquire brightness values of the plurality of regions in the synthetic ultrasound image 825 by respectively applying the weights to the N frequency band images.

A weight for a specific region in a specific frequency band image may be determined based on at least one of a noise level and a brightness level of the region. For example, as described with reference to FIG. 7, the ultrasound diagnosis apparatus 100 may acquire first image information regarding a region in the high-frequency band image, having a brightness level within the brightness range 704 that is greater than or equal to the first level 712 but less than the reference level 711. The ultrasound diagnosis apparatus 100 may set a weight for the first image information to be higher than a weight for image information regarding the low-frequency band image.

Referring to FIG. 8, $I_{ml}$ represents a brightness value at m-th row and l-th column in the synthetic ultrasound image 825. $w_{kmi}$ denotes a weight for a brightness value at the m-th row and l-th column in a k-th frequency band image. For example, $I_{11}$ may be calculated by using Equation (1). $I_{12}$ may be calculated by using Equation (2). $I_{44}$ may be calculated by using Equation (3). Brightness values for the other regions in the synthetic ultrasound image 825 may also be calculated in the same manner as above.

Figure 9:
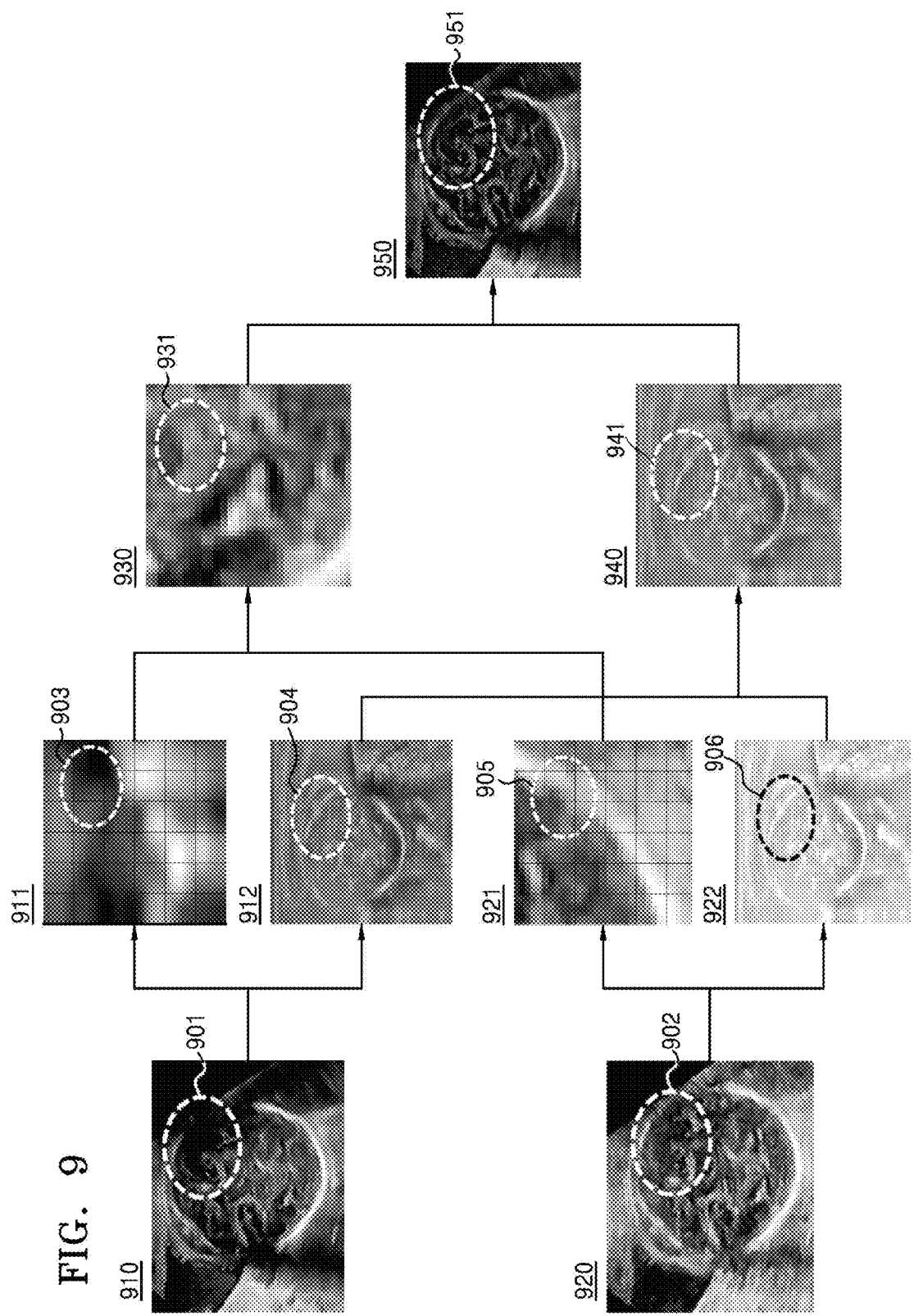
FIG. 9 is a diagram for explaining a process, performed by an ultrasound diagnosis apparatus, of acquiring a base image and a detail image for each of a plurality of frequency band images and synthesizing the plurality of frequency band images by using the acquired base images and detail images, according to an embodiment.

FIG. 9 is a diagram for explaining a process, performed by the ultrasound diagnosis apparatus 100, of acquiring a base image and a detail image for each of a plurality of frequency band images and synthesizing the plurality of frequency band images by using acquired base images and detail images, according to an embodiment.

The ultrasound diagnosis apparatus 100 may acquire, based on an ultrasound signal reflected from an object, high-frequency band images corresponding to high frequency bands and low-frequency band images corresponding to low frequency bands. For convenience, FIG. 9 shows only one of the high-frequency images and one of the low-frequency band images. The ultrasound diagnosis apparatus 100 may acquire a high-frequency band image 910 and a low-frequency band image 920 based on an ultrasound signal reflected from an object.

As shown in FIG. 9, a shadow region 901 in the high-frequency band image 910 does not accurately represent image information of the object. On the other hand, a region 902 in the low-frequency band image 920 may correspond to the shadow region 901 and represent image information of the object. Furthermore, the high-frequency band image 910 may clearly depict the object. On the other hand, the low-frequency band image 920 may not clearly depict an edge region of the object and include noise.

Thus, the ultrasound diagnosis apparatus 100 may acquire image information regarding a region that clearly depicts the object in the high-frequency band image 910 and image information regarding a region of the object that is not visible in the high-frequency band image 910.

In detail, the ultrasound diagnosis apparatus 100 may acquire a base image 911 in a high frequency band and a base image 921 in a low frequency band that represent brightness values for regions of the object by respectively performing spatial filtering on the high-and low-frequency band images 910 and 920. For example, the ultrasound diagnosis apparatus 100 may acquire the base images 911 and 921 in high-and low-frequency bands by respectively passing the high-and low-frequency band images 910 and 920 through an edge preserving filter.

Furthermore, the ultrasound diagnosis apparatus 100 may acquire a detail image 912 in the high frequency band, which represents details of regions of the object by removing the base image 911 in the high frequency band from the high-frequency band image 910. Similarly, the ultrasound diagnosis apparatus 100 may acquire a detail image 922 in the low frequency band by removing the base image 921 in the low frequency band from the low-frequency band image 920.

For a bright region in the base image 911 having a brightness level that is greater than or equal to a first level among brightness levels lower than a first reference level used as a reference in representing the brightness levels for the regions of the object, the ultrasound diagnosis apparatus 100 may set a weight for image information regarding the base image 911 in the high frequency band to be higher than a weight for image information regarding the base image 921 in the low frequency band. In this case, the first level may be a threshold level for brightness in the high frequency band, which allows for a predetermined level of noise. Thus, a region having a brightness level less than the first level may have a low sharpness level due to noise.

Furthermore, for a dark region in the base image 911 in the frequency band, which has a brightness level that is less than the first level among the brightness levels lower than the first reference level, the ultrasound diagnosis apparatus 100 may set a weight for image information regarding the base image 921 in the low-frequency band to be higher than a weight for image information regarding the base image 911 in the high frequency band. For example, the dark region in the base image 911 in the high frequency band, which has a brightness level less than the first level, may correspond to a region 903. The ultrasound diagnosis apparatus 100 may set a weight for image information regarding a region 905 in the base image 921 in the low frequency band to be higher than a weight for image information regarding the region 903 in the base image 911 in the high frequency band. In addition, because brightness in the low frequency band also has its threshold brightness level that allows for a predetermined level of noise, the ultrasound diagnosis apparatus 100 may acquire image information regarding a region having a brightness level that is greater than or equal to the threshold brightness level but less than the first level.

The ultrasound diagnosis apparatus 100 may generate a synthetic base image 930 by synthesizing the base image 911 in the high frequency band with the base image 921 in the low frequency band based on weights respectively set for regions in the base images 911 and 921.

For a bright region in the detail image 912 in the high frequency band, which has a detail level that is greater than or equal to a second level among detail levels lower than a second reference level used as a reference in representing sharpness levels for the regions of the object, the ultrasound diagnosis apparatus 100 may set a weight for image information regarding the detail image 912 in the high frequency band to be higher than a weight for image information regarding the detail image 922 in the low frequency band. In this case, the second level may be a threshold level for details in the high frequency band, which allows for a predetermined level of noise. Thus, a bright region having a detail level less than the second level may have a low sharpness level due to noise.

Furthermore, for a dark region in the detail image 912 in the high frequency band, which has a detail level that is less than the second level among the detail levels lower than the second reference level, the ultrasound diagnosis apparatus 100 may set a weight for image information regarding the detail image 922 in the low frequency band to be higher than a weight for image information regarding the detail image 912 in the high frequency band. For example, the dark region in the detail image 912 in the high frequency band, which has a detail level less than the second level, may correspond to a region 904. The ultrasound diagnosis apparatus 100 may set a weight for image information regarding a region 906 in the detail image 922 in the low frequency band to be higher than a weight for image information regarding the region 904 in the detail image 912 in the high frequency band. In addition, because details in the low frequency band also has its threshold detail level that allows for a predetermined level of noise, the ultrasound diagnosis apparatus 100 may acquire image information regarding a region having a detail level that is greater than or equal to the threshold detail level but less than the second level.

The ultrasound diagnosis apparatus 100 may generate a synthetic detail image 940 by synthesizing the detail image 912 in the high frequency band with the detail image 922 in the low frequency band based on weights respectively set for regions in the detail images 912 and 922.

The ultrasound diagnosis apparatus 1000 may generate a synthetic ultrasound image 950 by combining the synthetic base image 930 with the synthetic detail image 940. For example, a region 951 in the synthetic ultrasound image 950 may be generated by synthesizing a region 931 in the synthetic base image 930 with a region 941 in the synthetic detail image 940.

The ultrasound diagnosis apparatus 100 may generate the synthetic ultrasound image 950 to sharpen details that are not seen in bright or dark regions of an original ultrasound image.

Figure 10:
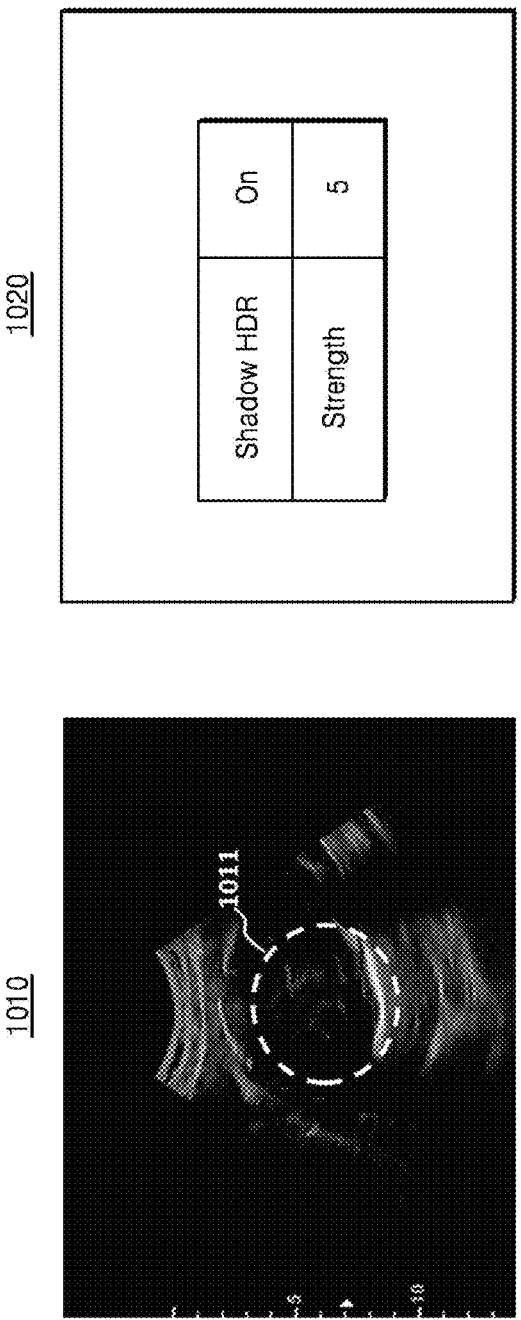
FIG. 10 is a diagram for explaining a process, performed by an ultrasound diagnosis apparatus, of receiving an input for adjusting a strength of a weight for specific image information and synthesizing a plurality of frequency band images according to the weight with the adjusted strength), according to an embodiment.

FIG. 10 is a diagram for explaining a process, performed by the ultrasound diagnosis apparatus 100, of receiving an input for adjusting a strength of a weight for specific image information and synthesizing a plurality of frequency band images according to the weight with the adjusted strength, according to an embodiment.

Referring to an image 1010 of FIG. 10, an ultrasound image displayed by the ultrasound diagnosis apparatus 100 may include a shadow region 1011 where a portion of an object is not clearly seen. The ultrasound diagnosis apparatus 100 may automatically detect the shadow region 1011 via analysis of the ultrasound image. Furthermore, the ultrasound diagnosis apparatus 100 may acquire the shadow region 1011 based on a user input.

The ultrasound diagnosis apparatus 100 may receive a command for performing a process of improving image quality for the shadow region 1011 and perform its operations described with reference to FIGS. 4 through 9 according to the command.

Referring to an image 1020 of FIG. 10, the ultrasound diagnosis apparatus 100 may receive an input of changing a "Shadow High Dynamic Range (HDR)" function to an on state via the UI device. In this case, the "Shadow HDR" function may be a function for sharpening the shadow region 1011 in the ultrasound image. Furthermore, although the function for sharpening the shadow region 1011 in the ultrasound image is indicated as the term "Shadow HDR" in FIG. 10, the function may be indicated as other terms.

According to the input for changing the "Shadow HDR" function to the on state, the ultrasound diagnosis apparatus 100 may perform an operation of correcting the shadow region 1011 in the ultrasound image. While performing the operation of correcting the shadow region 1011, the ultrasound diagnosis apparatus 100 may perform correction to improve not only a sharpness level of the shadow region 1011 but also the overall sharpness of the ultrasound image.

In addition, the ultrasound diagnosis apparatus 100 may receive, via a UI interface, an input for adjusting a strength of a weight to be applied to a low-frequency band image for synthesis of high- and low-frequency band images. For example, a strength of a weight may be adjustable from 0 to 10. When the strength of a weight is 0, a weight to be applied to a low-frequency band image is 0. When the strength of a weight is 10, a weight to be applied to a low-frequency band image is a maximum value of 10.

As shown in the image 1020 of FIG. 10, the ultrasound diagnosis apparatus 100 may receive, via the UI device, an input for adjusting a strength of a weight to be applied to a low-frequency band image to 5. The ultrasound diagnosis apparatus 100 may synthesize the high-and low-frequency band images according to the weight with the adjusted strength.

Furthermore, the ultrasound diagnosis apparatus 100 may receive, via the UI device, an input for setting a plurality of regions of interest (ROIs) in an ultrasound image as well as an input for respectively adjusting strengths of a weight to be applied to a low-frequency band image for the plurality of ROIs. The ultrasound diagnosis apparatus 100 may synthesize the high- and low-frequency band images based on weights with strengths respectively adjusted for the ROIs.

Figure 11:
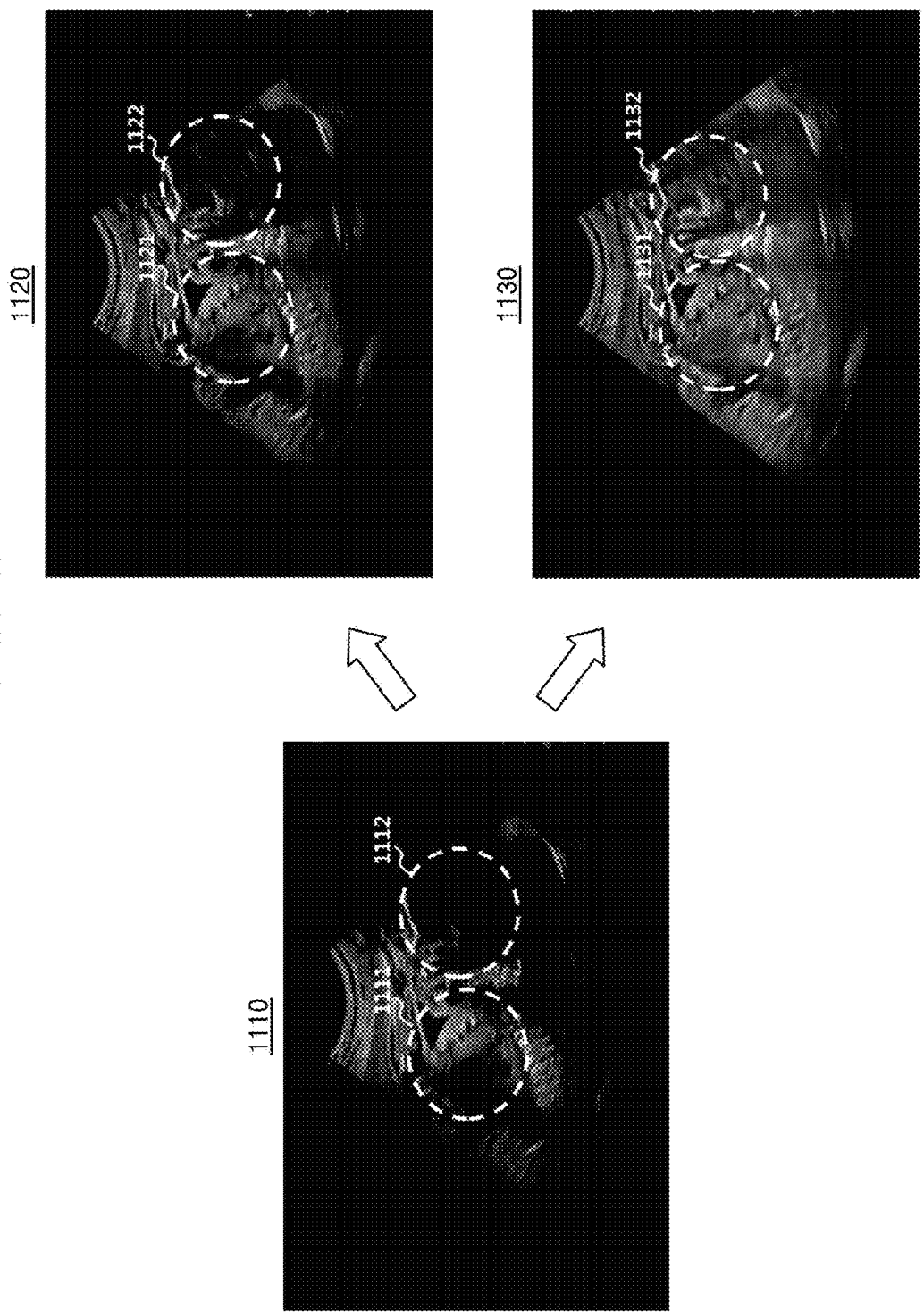
FIG. 11 is a diagram for explaining a synthetic ultrasound image obtained by an ultrasound diagnosis apparatus according to strengths of weights, according to an embodiment.

FIG. 11 is a diagram for explaining a synthetic ultrasound image obtained by the ultrasound diagnosis apparatus 100 according to strengths of weights, according to an embodiment.

An image 1110 of FIG. 11 is an ultrasound image obtained by the ultrasound diagnosis apparatus 100 when a "Shadow HDR" function is in an off state. As shown in the image 1110 of FIG. 11, the ultrasound image may include a dark region 1112 and a region 1111 where a region of an object is not well seen.

For example, the user may examine the ultrasound image displayed by the ultrasound diagnosis apparatus 100 and perform the "Shadow HDR" function. As shown in the image 1020 of FIG. 10, the user may adjust a strength of a weight to be applied to a low-frequency band image.

For example, an image 1120 of FIG. 11 may be a synthetic ultrasound image when a strength of a weight applied to the low-frequency band image is 5. On the other hand, an image 1130 of FIG. 11 may be a synthetic ultrasound image when a strength of a weight applied to the low-frequency band image is 10.

Detail levels for regions 1121 and 1122 in the image 1120 of FIG. 11 are respectively increased compared to detail levels for the regions 1111 and 1112 in the image 1110 of FIG. 11. Furthermore, a noise level for the region 1121 in the image 1120 is reduced compared to the region 1111 in the image 1110.

A detail level for a region 1132 in the image 1130 is increased compared to the detail level for the region 1112 in the image 1110. However, a detail level for a region 1131 in the image 1130 may be reduced compared to the detail level for the region 1111 due to an increase in noise. Furthermore, the detail levels for the regions 1131 in the image 1130 is reduced compared to the detail levels for the regions 1121 in the image 1120.

By comparing the image 1120 with the image 1130, it can be seen that the synthetic ultrasound image may have an improved quality when the strength of the weight to be applied to the low-frequency band image is adjusted to 5, compared to when the strength of the weight is adjusted to 10. Thus, when a "Shadow HDR" function is performed by the ultrasound diagnosis apparatus 100, a strength of a weight to be applied to a low-frequency band image needs to be adjusted properly.

The ultrasound diagnosis apparatus 100 may adjust a strength of a weight to be applied to a low-frequency band image to improve the quality of an ultrasound image by using attenuation characteristics of the low-frequency band image.

Figure 12:
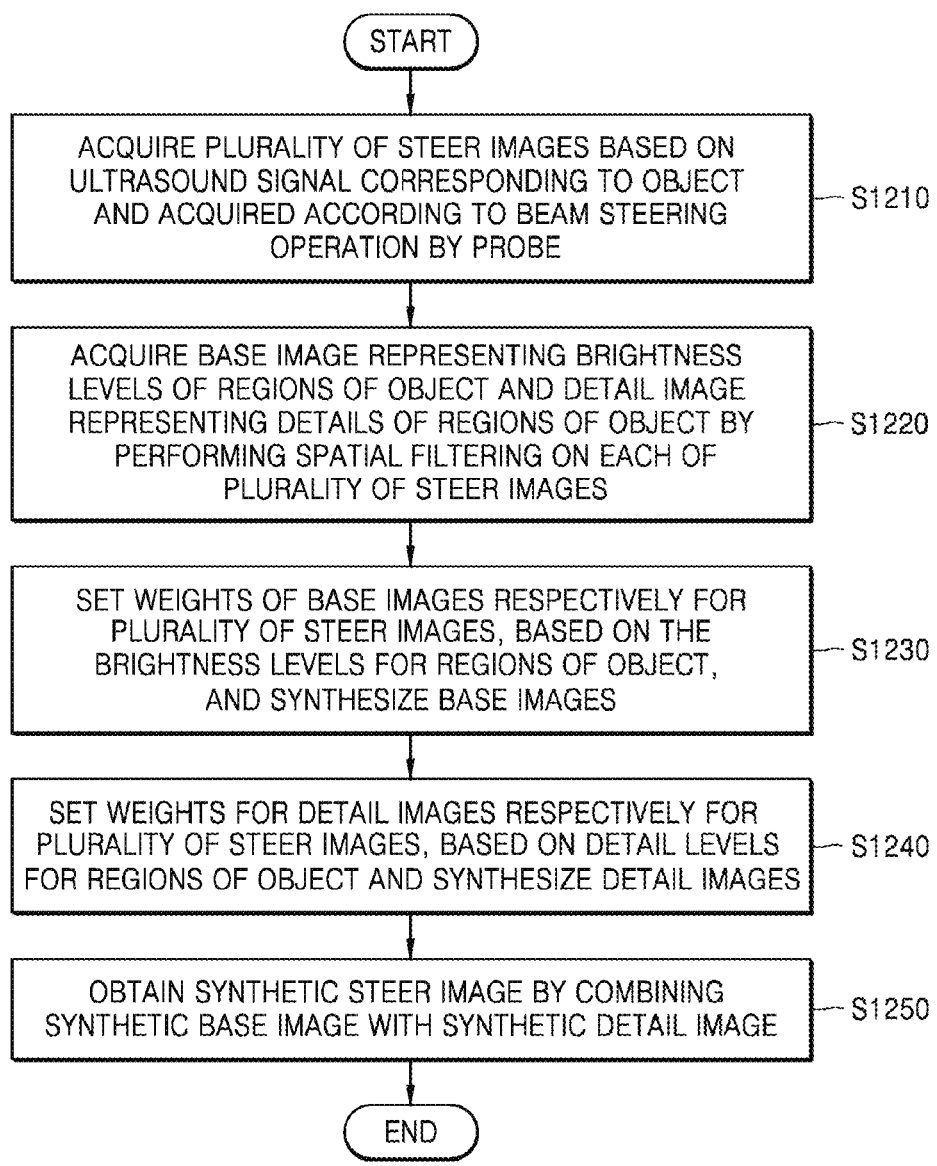
FIG. 12 is a flowchart of a method of operating an ultrasound diagnosis apparatus, according to an embodiment.

FIG. 12 is a flowchart of a method of operating the ultrasound diagnosis apparatus 100, according to an embodiment Referring to FIG. 12, the ultrasound diagnosis apparatus 100 may acquire a plurality of steer images based on an ultrasound signal corresponding to an object and acquired according to a beam steering operation by a probe (S1210).

The ultrasound diagnosis apparatus 100 may acquire a base image representing brightness levels of regions of the object and a detail image representing details of the regions of the object by performing spatial filtering on each of the plurality of steer images (S1220).

The ultrasound diagnosis apparatus 100 may respectively set weights of base images for the plurality of steer images, based on the brightness levels for the regions of the object (S1230). The ultrasound diagnosis apparatus 100 may also synthesize the base images for the plurality of steer images according to the weights respectively set for the base images. For example, the ultrasound diagnosis apparatus 100 may acquire a synthetic base image by respectively multiplying weights assigned to the base images by brightness values of the base images and adding the resulting products together. As another example, the ultrasound diagnosis apparatus 100 may select a base image having a maximum brightness value from among the base images for each region of the base image and acquire a synthetic base image by synthesizing selected base images.

The ultrasound diagnosis apparatus 100 may respectively set weights for detail images for the plurality of steer images, based on detail levels for the regions of the object (S1240). The ultrasound diagnosis apparatus 100 may also synthesize the detail images for the plurality of steer images according to the weights respectively set for the detail images. A method of synthesizing the detail images for the plurality of steer images may be substantially the same as the method of synthesizing the base images for the plurality of steer images in operation S1230.

The ultrasound diagnosis apparatus 100 may obtain a synthetic steer image by combining a synthetic base image with a synthetic detail image (S1250). The ultrasound diagnosis apparatus 100 may display the synthetic ultrasound image.

Figure 13:
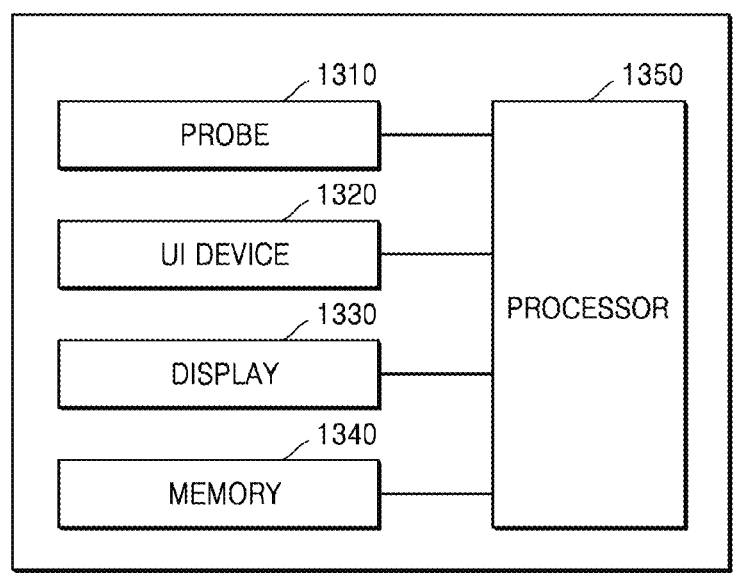
FIG. 13 is a block diagram of a configuration of an ultrasound diagnosis apparatus according to an embodiment.

FIG. 13 is a block diagram of a configuration of an ultrasound diagnosis apparatus 100 according to an embodiment.

Referring to FIG. 13, the ultrasound diagnosis apparatus 100 may include a probe 1310, a UI device 1320, a display 1330, a memory 1340, and a processor 1350. However, all the components shown in FIG. 13 are not essential components. The ultrasound diagnosis apparatus 100 may include more or fewer components than those shown in FIG. 13. Structures and operations of the components are now described in more detail. The ultrasound diagnosis apparatus 100 of FIG. 13 may correspond to the ultrasound diagnosis apparatus 100, 100a, 100b, or 100c described with reference to FIG. 1 or 2. Furthermore, the ultrasound diagnosis apparatus 100 of FIG. 13 may perform the operation methods described with reference to FIGS. 3 through 8.

The probe 1310 may include a plurality of transducers that convert ultrasound signals into electrical signals or vice versa. In other words, the probe 1310 may include a transducer array consisting of a plurality of transducers, and the plurality of transducers may be arranged in a one-dimensional (1D) or 2D array. Each of the plurality of transducers generates ultrasound signals separately or simultaneously. An ultrasound signal transmitted by each transducer is reflected off a discontinuous impedance surface within an object. Each transducer may convert a reflected echo signal into an electrical reception signal.

The UI device 1320 refers to a device via which data or signals for controlling the ultrasound diagnosis apparatus 100 are input by the user. The processor 1350 may control the display 1330 to generate and output a UI screen for receiving a predetermined command or data from the user.

The display 1330 displays a predetermined screen. In detail, the display 1330 may display a predetermined screen according to control by the processor 1350. The display 1330 includes a display panel (not shown) on which an image such as an ultrasound image may be displayed.

The memory 1340 may store a program for executing a method of operating the ultrasound diagnosis apparatus 100. Furthermore, the memory may store a code representing a method of operating the ultrasound diagnosis apparatus 100.

The processor 1350 may acquire a plurality of frequency band images respectively having different frequency bands based on an ultrasound signal corresponding to the object and acquired via the probe 1310.

For example, the processor 1350 may decompose the ultrasound signal according to a plurality of frequency bands. The processor 1350 may acquire, based on the decomposed ultrasound signal, a high-frequency band image corresponding to a predetermined high frequency band and a low-frequency band image corresponding to a predetermined low frequency band.

The processor 1350 may respectively determine weights for the plurality of frequency band images based on brightness values of regions including the object in each of the plurality of frequency band images.

For example, the processor 1350 may detect, in a high-frequency band image, a shadow region having a lower brightness level than a predetermined brightness level and a higher noise level than a predetermined noise level. The processor 1350 may acquire image information regarding a first region corresponding to the shadow region from a low-frequency band image. The processor may set a weight for the image information regarding the first region to be higher than a weight for image information regarding the shadow region in the high-frequency band image.

Furthermore, the processor 1350 may set a weight for image information regarding a non-shadow region in the high-frequency band image to be higher than a weight for image information regarding a second region in the low-frequency band image, corresponding to the non-shadow region.

For example, the processor 1350 may acquire a base image representing brightness levels for regions of the object and a detail image representing details of the regions of the object by performing spatial filtering on each of the plurality of frequency band images. The processor 1350 may set, based on brightness levels for the regions of the object, a weight for a base image in each of a plurality of frequency bands. Furthermore, the processor 1350 may set, based on detail levels of the regions of the object, a weight for a detail image in each of the plurality of frequency bands.

For example, the processor 1350 may receive, via the UI device 1320, an input for adjusting a strength of a weight for image information regarding a low-frequency band image among the plurality of frequency band images. The processor 1350 may adjust, based on the input for adjusting a strength of a weight, a weight for image information regarding a low-frequency band image.

The processor 1350 may synthesize the plurality of frequency band images based on the weights therefor.

For example, the processor 1350 may synthesize base images in the plurality of frequency bands according to weights respectively assigned to the base images. The processor 1350 may synthesize detail images in a plurality of frequency bands according to weights respectively assigned to the detail images. The processor 1350 may obtain a synthetic ultrasound image by combining a synthetic base image with a synthetic detail image.

As a specific example, for a bright region having a brightness level that is greater than or equal to a first level among brightness levels lower than a first reference level used as a reference in representing the brightness levels for the regions of the object, the processor 1350 may set a weight for image information regarding a base image for a high-frequency band image to be higher than a weight for image information regarding a base image for a low-frequency band image.

Furthermore, for a dark region having a brightness level that is less than the first level among brightness levels lower than the first reference level, the processor 1350 may set a weight for image information regarding a base image for a low-frequency band image to be higher than a weight for image information regarding a base image for a high-frequency band image.

The processor 1350 may generate a synthetic base image by synthesizing the base image for the high-frequency band image with the base image for the low-frequency band image, based on weights respectively set for regions in the base images.

For a bright region having a detail level that is greater than or equal to a second level among detail levels lower than a second reference level used as a reference in representing sharpness levels for the regions of the object, the processor 1350 may set a weight for image information regarding a detail image for the high-frequency band image to be higher than a weight for image information regarding a detail image for the low-frequency band image.

Furthermore, for a dark region having a detail level that is less than the second level among detail levels lower than the second reference level, the processor 1350 may set a weight for image information regarding the detail image for the low-frequency band image to be higher than a weight for image information regarding the detail image for the high-frequency band image.

The processor 1350 may generate a synthetic detail image by synthesizing the detail image for the high-frequency band image with the detail image for the low-frequency band image, based on weights respectively set for regions in the detail images. Then, the processor 1350 may generate a synthetic ultrasound image by combining the synthetic base image with the synthetic detail image.

As another example, the processor 1350 may synthesize the high- and low-frequency band images based on a weight for image information regarding the low-frequency band image, which is adjusted according to a user input.

The display 1330 may display a synthetic ultrasound image of the object generated as a result of the synthesis.

The display 1330 may display the synthetic ultrasound image and an original ultrasound image obtained based on the ultrasound signal. The display 1330 may display a result of comparing a sharpness or noise between the synthetic and original ultrasound images.

In addition, the processor 1350 may acquire a plurality of steer images based on an ultrasound signal corresponding to an object and acquired according to a beam steering operation by the probe 1310.

The processor 1350 may acquire a base image representing brightness levels of regions of the object and a detail image representing details of the regions of the object by performing spatial filtering on each of the plurality of steer images.

The processor 1350 may respectively set weights of base images for the plurality of steer images, based on the brightness levels for the regions of the object. The processor 1350 may synthesize the base images for the plurality of steer images according to the weights respectively set for the base images.

The processor 1350 may respectively set weights for detail images for the plurality of steer images, based on detail levels for the regions of the object. The processor 1350 may also synthesize the detail images for the plurality of steer images according to the weights respectively set for the detail images.

The processor 1350 may obtain a synthetic steer image by combining a synthetic base image with a synthetic detail image. The display 1330 may display the synthetic ultrasound image.

The ultrasound diagnosis apparatuses 100 described above may be implemented using hardware components, software components, and/or a combination thereof. For example, the apparatuses and components illustrated in the embodiments may be implemented using one or more general-purpose or special-purpose computers, such as a processor, a controller, an arithmetic logic unit (ALU), a digital signal processor, a microcomputer, a field programmable array (FPA), a programmable logic unit (PLU), a microprocessor, or any other device capable of responding to and executing instructions.

A processing device may run an operating system (OS) and one or more software applications running on the OS. The processing device may also access, store, manipulate, process, and create data in response to execution of software.

Although a single processing device may be illustrated for convenience, those of ordinary skill in the art will appreciate that a processing device may include a plurality of processing elements and/or a plurality of types of processing elements. For example, a processing device may include one or a plurality of processors and a controller. In addition, the processing device may have different processing configurations such as parallel processors.

Software may include a computer program, a piece of code, a command, or one or more combinations thereof and independently or collectively instruct or configure the processing device to operate as desired.

Software and/or data may be embodied permanently or temporarily in any type of machine, component, physical equipment, virtual equipment, computer storage medium or device, or in a transmitted signal wave so as to be interpreted by the processing device or to provide commands or data to the processing device. The software may also be distributed over network-coupled computer systems so that the software is stored and executed in a distributed fashion. The software and data may be stored in one or more computer-readable recording media.

The methods according to the embodiments may be implemented in the form of program instructions that may be executed through various computer devices and be recorded on non-transitory computer-readable recording media. The computer-readable recording media may also include, alone or in combination, program instructions, data files, data structures, and the like. The program instructions recorded on the non-transitory computer-readable recording media may be designed and configured specially for the embodiments or be known and available to those of ordinary skill in computer software.

Examples of non-transitory computer-readable recording media include magnetic media such as hard disks, floppy disks, and magnetic tape, optical media such as CD-ROM discs and DVDs, magneto-optical media such as floptical discs, and hardware devices that are specially configured to store and perform program instructions, such as ROM, RAM, flash memory, and the like.

Examples of program instructions include not only machine code made by a compiler but also high-level language code to be executed in a computer by using an interpreter.

The above-described hardware devices may be configured to act as one or more software modules in order to perform operations according to the embodiments, or vice versa.

While one or more embodiments have been described with reference to the figures, it will be understood by those of ordinary skill in the art that various modifications and changes in form and details may be made from the above descriptions without departing from the spirit and scope as defined by the following claims. For example, adequate effects may be achieved even if the above techniques are performed in a different order than that described above, and/or the aforementioned elements, such as systems, structures, devices, or circuits, are combined or coupled in different forms and modes than those described above or are replaced or supplemented by other components or their equivalents.

Thus, the scope of the disclosure is defined not by the above-described embodiments but by the appended claims and their equivalents.

What is claimed is:

1. A method of operating an ultrasound diagnosis apparatus, the method comprising:
acquiring a plurality of frequency band images including a first frequency band image having a first frequency band higher than a first reference frequency and a second frequency band image having a second frequency band lower than a second reference frequency that is lower than the first reference frequency based on an ultrasound signal corresponding to an object;

determining a base image representing brightness levels for regions of the object and a detail image representing details of the regions of the object by respectively performing spatial filtering on each of the plurality of frequency band images, determining weights respectively for the plurality of frequency band images;

synthesizing the plurality of frequency band images based on the weights for the plurality of frequency band images; and displaying a synthetic ultrasound image of the object, generated as a result of the synthesizing, wherein the determining of the weights comprises:

setting a weight for image information regarding a region corresponding to a shadow region, which is acquired from the second frequency band image, to be higher than a weight for image information regarding the shadow region in the first frequency band image, setting weights for the base images respectively corresponding to a plurality of frequency bands, based on the brightness levels for the regions of the object; and setting weights for the detail images respectively corresponding to the plurality of frequency bands, based on detail levels representing sharpness for the regions of the object.

2. The method of claim 1, wherein the acquiring of the plurality of frequency band images comprises
classifying the ultrasound signal into a plurality of ultrasound signals by dividing it into a plurality of frequency band sections and acquiring, based on the classified ultrasound signal, the first frequency band image and the second frequency band image.

3. The method of claim 2, wherein the determining of the weights respectively for the plurality of frequency band images comprises:

detecting, in the first frequency band image, the shadow region having a lower brightness level than a predetermined brightness level and a higher noise level than a predetermined noise level.

4. The method of claim 3, wherein the determining of the weights for the plurality of frequency band images comprises
setting a weight for image information regarding a non-shadow region in the first frequency band image to be higher than a weight for image information regarding a region in the second frequency band image corresponding to the non-shadow region.

5. The method of claim 1, wherein the synthesizing of the plurality of frequency band images comprises:

synthesizing the base images respectively corresponding to the plurality of frequency bands according to the weights set for the base images;

synthesizing the detail images respectively corresponding to the plurality of frequency bands according to the weights set for the detail images or the brightness level of the base images; or synthesizing the detail images based on a maximum absolute value determined for each region of a detail image; and obtaining the synthetic ultrasound image by combining a synthetic base image acquired by the synthesizing of the base images with a synthetic detail image acquired by the synthesizing of the detail images.

6. The method of claim 1, wherein the setting of the weights for the base images respectively corresponding to the plurality of frequency bands based on the brightness levels for the regions of the object comprises:

setting, for a bright region having a brightness level that is greater than or equal to a first level among brightness levels lower than a first reference level used as a reference in representing the brightness levels for the regions of the object, a weight for image information regarding a base image for a first frequency band image to be higher than a weight for image information regarding a base image for a second frequency band image; and setting, for a dark region having a brightness level that is less than the first level among the brightness levels lower than the first reference level, the weight for the image information regarding the base image for the second frequency band image to be higher than the weight for the image information regarding the base image for the first frequency band image.

7. The method of claim 1, wherein the setting of the weights for the detail images respectively corresponding to the plurality of frequency bands based on the detail levels for the regions of the object comprises:

setting, for a bright region having a detail level that is greater than or equal to a second level among detail levels lower than a second reference level used as a reference in representing sharpness levels for the regions of the object, a weight for image information regarding a detail image for a first frequency band image to be higher than a weight for image information regarding a detail image for a second frequency band image; and setting, for a dark region having a detail level that is less than the second level among the detail levels lower than the second reference level, the weight for the image information regarding the detail image for the second frequency band image to be higher than the weight for the image information regarding the detail image for the first frequency band image.

8. The method of claim 1, further comprising
receiving an input for adjusting a strength of a weight for image information regarding a second frequency band image among the plurality of frequency band images, wherein the synthesizing of the plurality of frequency band images comprises synthesizing the plurality of frequency band images based on the weight with the adjusted strength for the image information regarding the second frequency band image.

9. The method of claim 1, wherein the displaying of the synthetic ultrasound image of the object comprises:

displaying the synthetic ultrasound image and an original ultrasound image obtained based on the ultrasound signal; and displaying a result of comparing a sharpness level or noise level between the synthetic ultrasound image and the original ultrasound image.

10. A method of operating an ultrasound diagnosis apparatus, the method comprising:

acquiring a plurality of steer images based on an ultrasound signal corresponding to an object and acquired according to a beam steering operation by a probe;

determining a base image representing brightness levels of regions of the object and a detail image representing details of the regions of the object by respectively performing spatial filtering on each of the plurality of steer images;

setting weights of the base images respectively for the plurality of steer images, based on the brightness levels for the regions of the object, and synthesizing the base images;

setting weights for the detail images respectively for the plurality of steer images, based on detail levels representing sharpness for the regions of the object, and synthesizing the detail images;

displaying a synthetic steer image obtained by combining a synthetic base image acquired by the synthesizing of the base images with a synthetic detail image acquired by the synthesizing of the detail images; and receiving an input for adjusting a strength of a weight for image information regarding a predetermined steer image among the plurality of steer images, wherein the synthesizing of the base images and the detail images comprises synthesizing the base images and the detail images based on the weight with the adjusted strength for the image information regarding the predetermined steer image.

11. An ultrasound diagnosis apparatus comprising:

a probe configured to transmit an ultrasound signal to an object and receive an ultrasound signal reflected from the object;

a processor configured to:

acquire a plurality of frequency band images including a first frequency band image having a predetermined high frequency band higher than a first frequency and a second frequency band image having a predetermined low frequency band lower than a second frequency lower than the first frequency based on the reflected ultrasound signal, determine a base image representing brightness levels for regions of the object and a detail image representing details of the regions of the object by respectively performing spatial filtering on each of the plurality of frequency band images, determine weights respectively for the plurality of frequency band images, and generate a synthetic ultrasound image of the object by synthesizing the plurality of frequency band images based on the weights for the plurality of frequency band images; and a display displaying the synthetic ultrasound image, wherein the processor is further configured to:

set a weight for image information regarding a region corresponding to a shadow region, which is acquired from the second frequency band image, to be higher than a weight for image information regarding the shadow region in the first frequency band image;

set weights for the base images respectively corresponding to a plurality of frequency bands, based on the brightness levels for the regions of the object; and set weights for the detail images respectively corresponding to the plurality of frequency bands, based on detail levels representing sharpness for the regions of the object.

12. The ultrasound diagnosis apparatus of claim 11, wherein the processor is further configured to classify the ultrasound signal into a plurality of ultrasound signals by dividing it into a plurality of frequency band sections and acquire, based on the classified ultrasound signal, the first frequency band image and the second frequency band image.

13. The ultrasound diagnosis apparatus of claim 12, wherein the processor is further configured to:

detect, in the first frequency band image, the shadow region having a lower brightness level than a predetermined brightness level and a higher noise level than a predetermined noise level.

14. The ultrasound diagnosis apparatus of claim 11, wherein the processor is further configured to:

synthesize the base images respectively corresponding to the plurality of frequency bands according to the weights set for the base images;

synthesize the detail images respectively corresponding to the plurality of frequency bands according to the weights set for the detail images or the brightness level of the base images; or synthesize the detail images based on a maximum absolute value determined for each region of a detail image; and obtain the synthetic ultrasound image by combining a synthetic base image acquired by the synthesizing of the base images with a synthetic detail image acquired by the synthesizing of the detail images.

15. The ultrasound diagnosis apparatus of claim 11, wherein the processor is further configured to:

set, for a bright region having a brightness level that is greater than or equal to a first level among brightness levels lower than a first reference level used as a reference in representing the brightness levels for the regions of the object, a weight for image information regarding a base image for a first frequency band image to be higher than a weight for image information regarding a base image for a second frequency band image; and set, for a dark region having a brightness level that is less than the first level among the brightness levels lower than the first reference level, the weight for the image information regarding the base image for the second frequency band image to be higher than the weight for the image information regarding the base image for the first frequency band image.

16. The ultrasound diagnosis apparatus of claim 11, wherein the processor is further configured to: set, for a bright region having a detail level that is greater than or equal to a second level among detail levels lower than a second reference level used as a reference in representing sharpness levels for the regions of the object, a weight for image information regarding a detail image for a first frequency band image to be higher than a weight for image information regarding a detail image for a second frequency band image; and set, for a dark region having a detail level that is less than the second level among the detail levels lower than the second reference level, the weight for the image information regarding the detail image for the second frequency band image to be higher than the weight for the image information regarding the detail image for the first frequency band image.

17. The ultrasound diagnosis apparatus of claim 11, further comprising a user interface device configured to receive an input for adjusting a strength of a weight for image information regarding a second frequency band image among the plurality of frequency band images, wherein the processor is further configured to synthesize the plurality of frequency band images based on the weight with the adjusted strength for the image information regarding the second frequency band image.

* * * * *